(12) United States Patent
Bodner et al.

(10) Patent No.: US 10,639,489 B2
(45) Date of Patent: May 5, 2020

(54) LEADLESS CARDIAC STIMULATION DEVICE EMPLOYING DISTRIBUTED LOGIC

(71) Applicant: CARDIAC PACEMAKERS, INC., St. Paul, MN (US)

(72) Inventors: Jeffrey P. Bodner, St. Paul, MN (US); Randy Bierwerth, Woodbury, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 21 days.

(21) Appl. No.: 15/871,672

(22) Filed: Jan. 15, 2018

(65) Prior Publication Data

US 2018/0154164 A1 Jun. 7, 2018

Related U.S. Application Data

(63) Continuation of application No. 15/601,662, filed on May 22, 2017, which is a continuation of application
(Continued)

(51) Int. Cl.
*A61N 1/36* (2006.01)
*A61N 1/39* (2006.01)
(Continued)

(52) U.S. Cl.
CPC ........... *A61N 1/3987* (2013.01); *A61N 1/056* (2013.01); *A61N 1/0587* (2013.01); *A61N 1/368* (2013.01);
(Continued)

(58) Field of Classification Search
CPC .............. A61N 1/3987; A61N 1/37235; A61N 1/3684; A61N 1/3962; A61N 1/36514;
(Continued)

(56) References Cited

U.S. PATENT DOCUMENTS 3,835,864 A 9/1974 Rasor et al.
3,943,936 A 3/1976 Rasor et al.
(Continued)

FOREIGN PATENT DOCUMENTS

| JP | 5059618 B2 | 10/2012 |
| WO | 2004002572 A1 | 1/2004 |
| WO | 2004012811 A1 | 2/2004 |

OTHER PUBLICATIONS

JP Office Action dated Jun. 28, 2011 for JP Application No. 2007-546668, 6 pgs.
(Continued)

*Primary Examiner* — Allen Porter
*Assistant Examiner* — Natasha Patel
(74) *Attorney, Agent, or Firm* — Seager, Tufte & Wickhem LLP

(57) ABSTRACT

Systems and methods involve an intrathoracic cardiac stimulation device operable to provide autonomous cardiac sensing and energy delivery. The cardiac stimulation device includes a housing configured for intrathoracic placement relative to a patient's heart. A fixation arrangement of the housing is configured to affix the housing at an implant location within cardiac tissue or cardiac vasculature. An electrode arrangement supported by the housing is configured to sense cardiac activity and deliver stimulation energy to the cardiac tissue or cardiac vasculature. Energy delivery circuitry in the housing is coupled to the electrode arrangement. Detection circuitry is provided in the housing and coupled to the electrode arrangement. Communications circuitry may optionally be supported by the housing. A controller in the housing coordinates delivery of energy to the cardiac tissue or cardiac vasculature in accordance with an energy delivery protocol appropriate for the implant location.

19 Claims, 6 Drawing Sheets

Related U.S. Application Data

No. 14/450,914, filed on Aug. 4, 2014, now Pat. No. 9,889,312, which is a continuation of application No. 11/014,105, filed on Dec. 16, 2004, now Pat. No. 8,818,504.

(51) Int. Cl.

| | | |
|---|---|---|
| *A61N 1/368* | (2006.01) | |
| *A61N 1/365* | (2006.01) | |
| *A61N 1/372* | (2006.01) | |
| *A61N 1/05* | (2006.01) | |
| *A61N 1/375* | (2006.01) | |
| *A61N 1/378* | (2006.01) | |

(52) U.S. Cl.
CPC ....... *A61N 1/3684* (2013.01); *A61N 1/36514* (2013.01); *A61N 1/375* (2013.01); *A61N 1/3756* (2013.01); *A61N 1/3787* (2013.01); *A61N 1/37235* (2013.01); *A61N 1/3962* (2013.01); *A61N 1/37205* (2013.01); *A61N 1/37288* (2013.01)

(58) Field of Classification Search
CPC .... A61N 1/3756; A61N 1/368; A61N 1/3787; A61N 1/375; A61N 1/0587; A61N 1/056; A61N 1/37288; A61N 1/37205
See application file for complete search history.

(56) References Cited

U.S. PATENT DOCUMENTS

| | | |
|---|---|---|
| 4,157,720 A | 6/1979 | Greatbatch |
| 4,256,115 A | 3/1981 | Bilitch |
| 4,562,841 A | 1/1986 | Brockway et al. |
| 4,787,389 A | 11/1988 | Tarjan |
| 4,819,662 A | 4/1989 | Heil, Jr. et al. |
| 4,928,688 A | 5/1990 | Mower |
| 5,036,849 A | 8/1991 | Hauck et al. |
| 5,133,353 A | 7/1992 | Hauser |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,284,136 A | 2/1994 | Hauck et al. |
| 5,301,677 A | 4/1994 | Hsung |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,334,222 A | 8/1994 | Salo et al. |
| 5,372,606 A | 12/1994 | Lang et al. |
| 5,376,106 A | 12/1994 | Stahmann et al. |
| 5,388,578 A | 2/1995 | Yomtov et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,468,254 A | 11/1995 | Hahn et al. |
| 5,540,727 A | 7/1996 | Tockman et al. |
| 5,545,186 A | 8/1996 | Olson et al. |
| 5,620,466 A | 4/1997 | Haefner et al. |
| 5,634,938 A | 6/1997 | Swanson et al. |
| 5,662,688 A | 9/1997 | Haefner et al. |
| 5,792,203 A | 8/1998 | Schroeppel |
| 5,814,089 A | 9/1998 | Stokes et al. |
| 5,836,987 A | 11/1998 | Baumann et al. |
| 5,855,593 A | 1/1999 | Olson et al. |
| 6,026,320 A | 2/2000 | Carlson et al. |
| 6,044,298 A | 3/2000 | Salo et al. |
| 6,055,454 A | 4/2000 | Heemels |
| 6,141,581 A | 10/2000 | Olson et al. |
| 6,141,588 A | 10/2000 | Cox et al. |
| 6,164,284 A | 12/2000 | Schulman et al. |
| 6,208,894 B1 | 3/2001 | Schulman et al. |
| 6,221,011 B1 | 4/2001 | Bardy |
| 6,240,316 B1 | 5/2001 | Richmond et al. |
| 6,259,947 B1 | 7/2001 | Olson et al. |
| 6,270,457 B1 | 8/2001 | Bardy |
| 6,277,072 B1 | 8/2001 | Bardy |
| 6,280,380 B1 | 8/2001 | Bardy |
| 6,285,907 B1 | 9/2001 | Kramer et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,409,674 B1 | 6/2002 | Brockway et al. |
| 6,411,848 B2 | 6/2002 | Kramer et al. |
| 6,424,865 B1 | 7/2002 | Ding |
| 6,438,410 B2 | 8/2002 | Hsu et al. |
| 6,440,066 B1 | 8/2002 | Bardy |
| 6,445,953 B1 | 9/2002 | Bulkes et al. |
| 6,459,929 B1 | 10/2002 | Hopper et al. |
| 6,487,443 B2 | 11/2002 | Olson et al. |
| 6,542,775 B2 | 4/2003 | Ding et al. |
| 6,564,807 B1 | 5/2003 | Schulman et al. |
| 6,597,951 B2 | 7/2003 | Kramer et al. |
| 6,631,290 B1 | 10/2003 | Guck et al. |
| 7,069,075 B2 | 6/2006 | Olson |
| 7,383,085 B2 | 6/2008 | Olson |
| 7,937,148 B2 | 5/2011 | Jacobson |
| 8,315,701 B2 | 11/2012 | Cowan et al. |
| 8,744,572 B1 | 6/2014 | Greenhut et al. |
| 2004/0147973 A1* | 7/2004 | Hauser ................ A61N 1/056 607/36 |
| 2005/0055056 A1 | 3/2005 | Olson |
| 2006/0085039 A1* | 4/2006 | Hastings ............. A61N 1/0587 607/9 |
| 2006/0135999 A1 | 6/2006 | Bodner et al. |
| 2007/0088396 A1* | 4/2007 | Jacobson ............. A61N 1/3708 607/9 |
| 2007/0088405 A1 | 4/2007 | Jacobson |
| 2011/0208260 A1 | 8/2011 | Jacobson |
| 2013/0041422 A1 | 2/2013 | Jacobson |
| 2013/0282073 A1 | 10/2013 | Cowan et al. |
| 2013/0325081 A1 | 12/2013 | Karst et al. |
| 2014/0214104 A1 | 7/2014 | Greenhut et al. |
| 2014/0214105 A1 | 7/2014 | DeGroot et al. |

OTHER PUBLICATIONS

JP Office Action dated Feb. 28, 2012 for JP Application No. 2007-546668, 4 pgs.

JP Office Action Response dated Jun. 27, 2012 for JP Application No. 2007-54668, 15 pgs.

All Non-Patent Literature documents and foreign patent documents have been previously uploaded in parent U.S. Appl. No. 11/014,105, filed Dec. 16, 2004.

\* cited by examiner

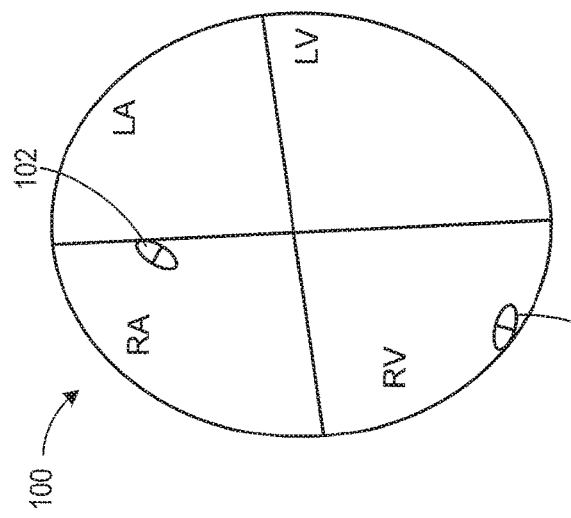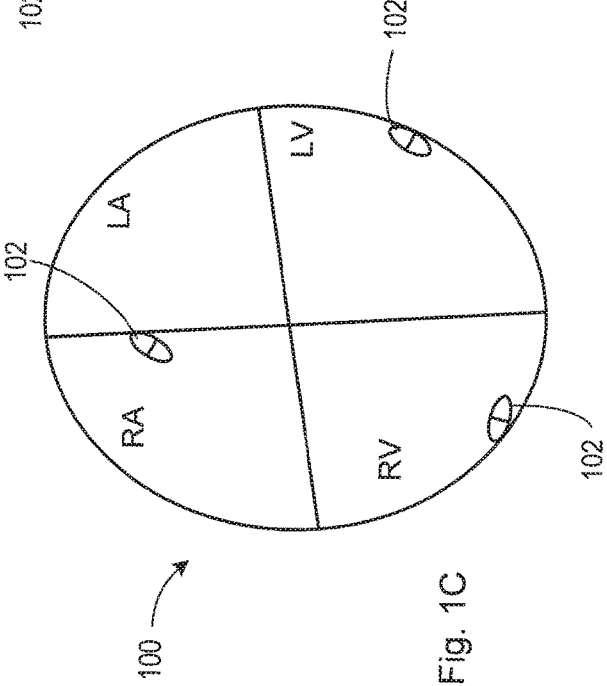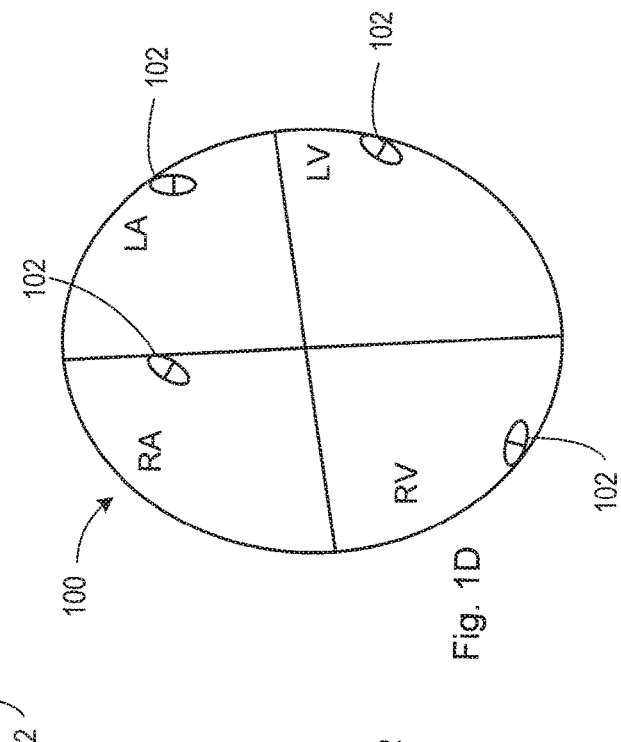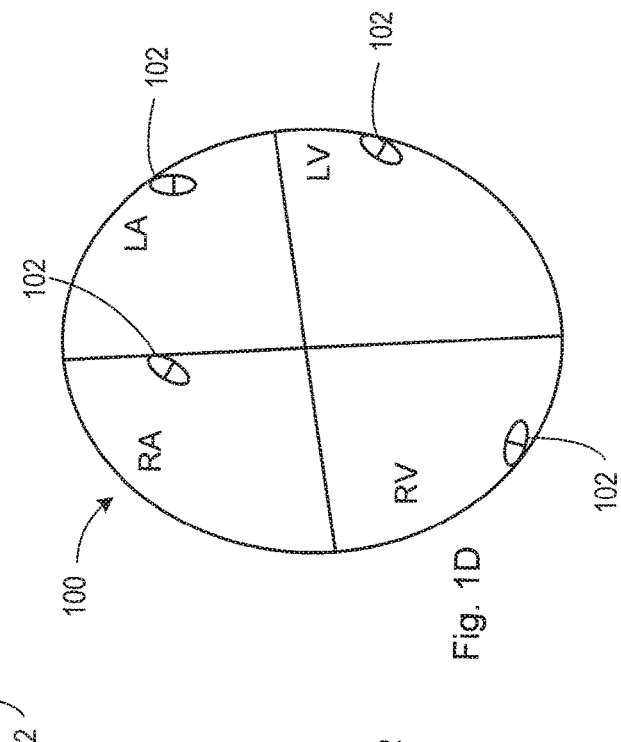

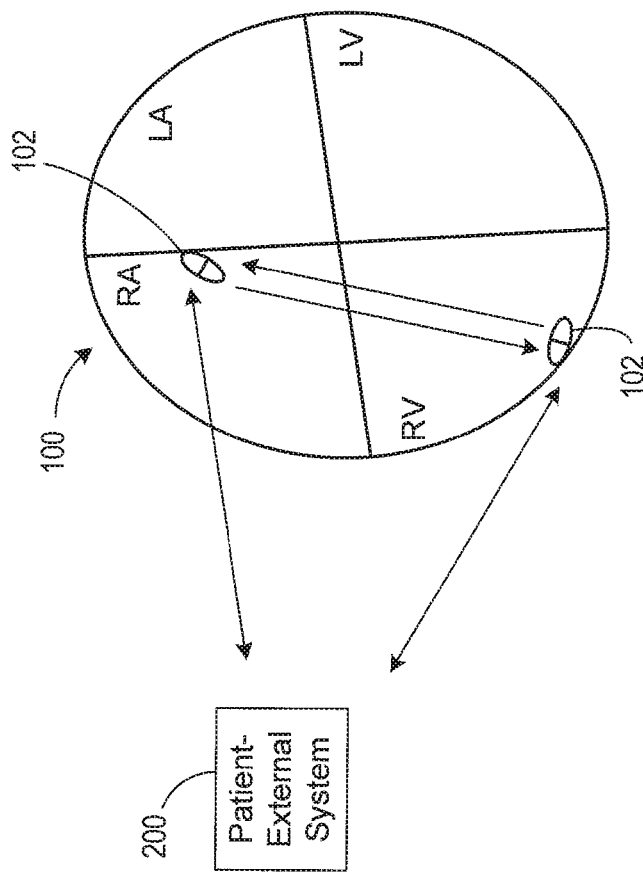
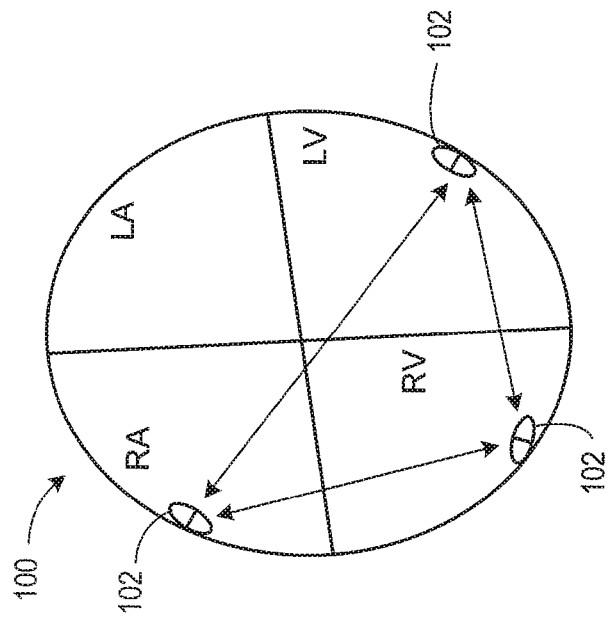

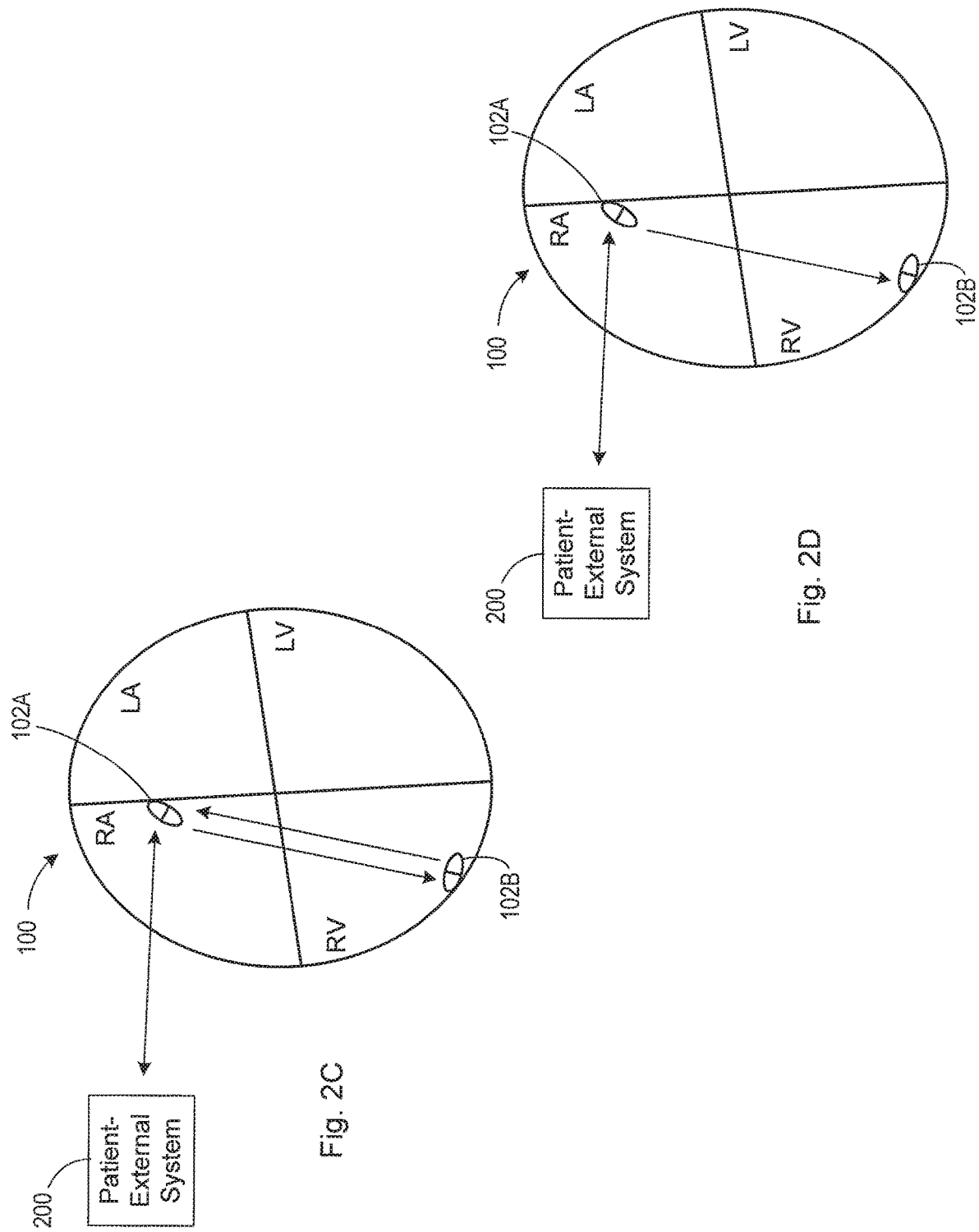

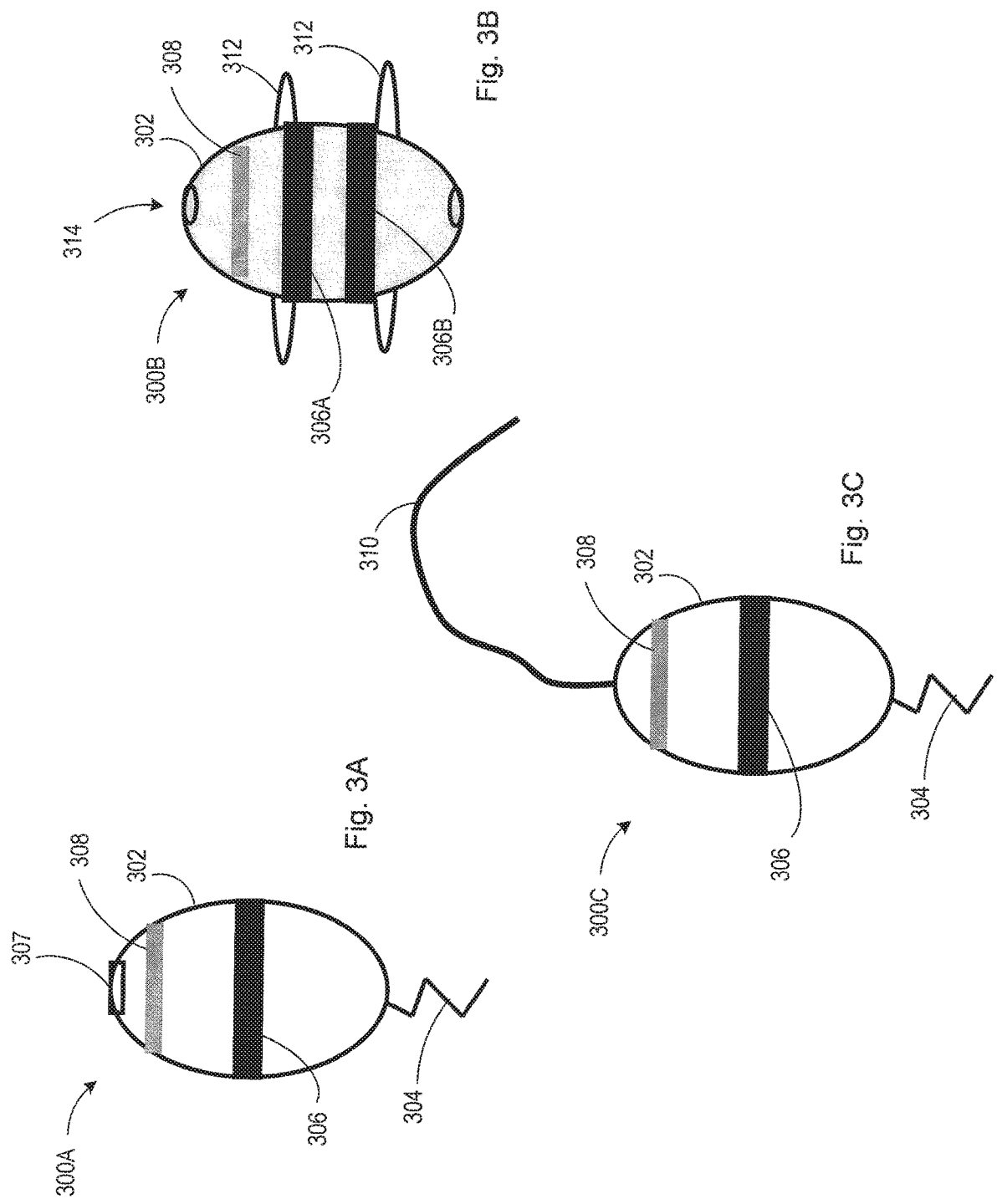

LEADLESS CARDIAC STIMULATION DEVICE EMPLOYING DISTRIBUTED LOGIC

RELATED APPLICATION DATA

This application is a continuation of U.S. application Ser. No. 15/601,662, filed May 22, 2017, which is a continuation of U.S. application Ser. No. 14/450,914, filed Aug. 4, 2014, which is a continuation of U.S. application Ser. No. 11/014,105, filed Dec. 16, 2004, now U.S. Pat. No. 8,818,504, the disclosures of which are incorporated herein by reference.

FIELD OF THE INVENTION

The present invention relates generally to implantable medical devices and, more particularly, to leadless systems and methods for detecting cardiac activity and treating adverse cardiac conditions.

BACKGROUND OF THE INVENTION

The healthy heart produces regular, synchronized contractions. Rhythmic contractions of the heart are normally initiated by the sinoatrial (SA) node, which are specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and may be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating the arrhythmias described above.

Such implantable cardiac rhythm management systems include pacemakers and implantable cardioverter/defibrillators. A typical ICD, for example, includes one or more endocardial leads to which at least one defibrillation electrode is connected. Such ICDs are capable of delivering high-energy shocks to the heart, interrupting the ventricular tachyarrythmia or ventricular fibrillation, and allowing the heart to resume normal sinus rhythm. ICDs may also include pacing functionality.

SUMMARY OF THE INVENTION

The present invention is directed to systems and methods that provide for detection of cardiac activity using a distributed logic approach. Embodiments of the invention are also directed to methods and devices that further provide for energy delivery to cardiac tissue using a distributed logic approach. Embodiments of the invention are also directed to leadless cardiac sensing and/or energy delivery devices, including those that are implantable in, on, or about the heart.

According to embodiments of the present invention, an intrathoracic cardiac stimulation device is operable to provide autonomous cardiac sensing and energy delivery. The cardiac stimulation device includes a housing configured for intrathoracic placement relative to a patient's heart. A fixation arrangement is supported by the housing and configured to affix the housing at an implant location within cardiac tissue or cardiac vasculature. An electrode arrangement is supported by the housing and configured to sense cardiac activity and deliver stimulation energy to the cardiac tissue or cardiac vasculature.

Energy delivery circuitry is provided in the housing and coupled to the electrode arrangement. Detection circuitry is provided in the housing and coupled to the electrode arrangement. A controller is provided in the housing and coupled to the energy delivery circuitry and detection circuitry. The controller coordinates delivery of energy to the cardiac tissue or cardiac vasculature in accordance with an energy delivery protocol appropriate for the implant location. Optional communications circuitry may be supported by the housing to effect communications between plural intrathoracic cardiac stimulation devices and/or a patient-external system.

According to other embodiments, a cardiac system includes two or more of such intrathoracic cardiac stimulation devices. Each of the cardiac stimulation devices is configured for intrathoracic placement relative to the patient's heart. The controller of each cardiac stimulation device coordinates delivery of energy in accordance with an energy delivery protocol appropriate for the implant location at which the particular cardiac stimulation device is affixed.

In accordance with further embodiments, an intrathoracic cardiac stimulation method involves sensing cardiac activity from each of a plurality of intrathoracic locations, and delivering, from the plurality of intrathoracic locations, energy to cardiac tissue or cardiac vasculature responsive to the sensed cardiac activity. The method further involves coordinating, at the plurality of intrathoracic locations, the energy delivery in accordance with a distributed energy delivery protocol. In other embodiments, the method may further involve establishing a communication link between the plurality of intrathoracic locations, and coordinating, via the communication link, the energy delivery from each of the plurality of intrathoracic locations in accordance with an energy delivery protocol.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 1A is a depiction of a heart, with an intrathoracic cardiac stimulation device implanted in a single chamber of the heart in accordance with an embodiment of the present invention;

FIG. 1B is a depiction of a heart, with an intrathoracic cardiac stimulation device implanted in two chambers of the heart (e.g., dual chamber configuration) in accordance with an embodiment of the present invention;

FIG. 1C is a depiction of a heart, with an intrathoracic cardiac stimulation device implanted in three chambers of the heart (e.g., bi-ventricular or resynchronization configurations) in accordance with an embodiment of the present invention;

FIG. 1D is a depiction of a heart, with an intrathoracic cardiac stimulation device implanted in each of the four chambers of the heart (e.g., bi-ventricular or resynchronization configurations) in accordance with an embodiment of the present invention;

FIG. 2A depicts communication linkage between multiple intrathoracic cardiac stimulation devices that provides for coordinated energy delivery to the heart in accordance with an embodiment of the present invention;

FIG. 2B depicts bi-directional communication linkage between multiple intrathoracic cardiac stimulation devices that provides for coordinated energy delivery to the heart, FIG. 2B further showing communication linkage between each of the cardiac stimulation devices and a patient-external system in accordance with an embodiment of the present invention;

FIG. 2C depicts bi-directional communication linkage between multiple intrathoracic cardiac stimulation devices that provides for coordinated energy delivery to the heart, FIG. 2C further showing communication linkage between one of the cardiac stimulation devices and a patient-external system in accordance with an embodiment of the present invention;

FIG. 2D depicts uni-directional communication linkage between multiple intrathoracic cardiac stimulation devices that provides for coordinated energy delivery to the heart, FIG. 2D further showing communication linkage between one of the cardiac stimulation devices and a patient-external system in accordance with an embodiment of the present invention;

FIG. 3A illustrates an intrathoracic cardiac stimulation device configured for endocardial or epicardial implantation that provides cardiac pacing therapy in accordance with an embodiment of the present invention;

FIG. 3B illustrates an intrathoracic cardiac stimulation device configured for transvenous implantation that provides cardiac pacing therapy in accordance with an embodiment of the present invention;

FIG. 3C illustrates an intrathoracic cardiac stimulation device configured for endocardial or epicardial implantation that provides one or both of cardiac defibrillation and cardioversion therapy, alone or with pacing therapy, in accordance with an embodiment of the present invention;

Figure 4:
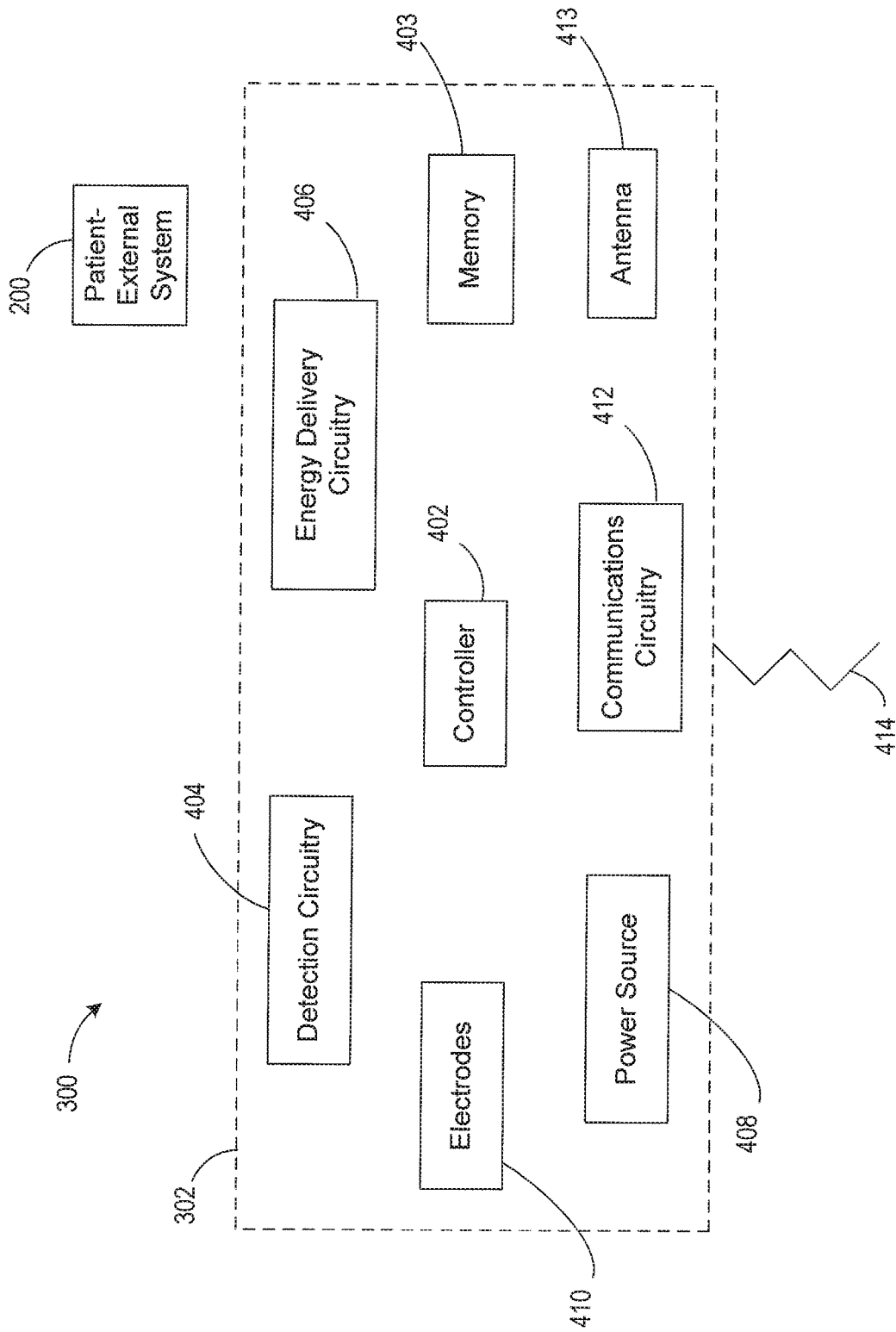
FIG. 4 is a block diagram of electronic circuitry and components of an intrathoracic cardiac stimulation device in accordance with an embodiment of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device according to the present invention may include one or more of the features, structures, methods, or combinations thereof described hereinbelow. For example, a cardiac monitor or a cardiac stimulator may be implemented to include one or more of the advantageous features and/or processes described below. It is intended that such a monitor, stimulator, or other implantable device need not include all of the features described herein, but may be implemented to include selected features that provide for useful structures and/or functionality. Such a device may be implemented to provide a variety of therapeutic or diagnostic functions.

Embodiments of the invention are directed to methods and devices that provide for detection of cardiac activity using a distributed logic approach. Embodiments of the invention are also directed to methods and devices that provide for energy delivery to cardiac tissue using a distributed logic approach. Embodiments of the invention are further directed to methods and devices that provide for treatment of adverse cardiac conditions, such as by provision of one or more of pacing, resynchronization, and defibrillation/cardioversion therapies, using a distributed logic approach. Embodiments of the invention are further directed to leadless cardiac sensing and/or energy delivery devices, including those that are implantable in, on, or about the heart.

In accordance with various embodiments, a cardiac stimulation system of the present invention includes one or more cardiac stimulation devices, each of which provides for cardiac activity sensing and delivery of energy to cardiac tissue. Although such cardiac stimulation devices are preferably implemented for intrathoracic placement relative to a patient's heart, it is understood that a cardiac stimulation system of the present invention may provide for coordinated cardiac sensing and/or energy delivery using one or more cardiac stimulation devices placed outside of the rib cage, such as at one or more subcutaneous, non-intrathoracic locations. Further, although it will be appreciated that a leadless intrathoracic cardiac stimulation system provides a number of advantages over lead-based implementations, benefits provided by a distributed logic approach of the present invention may be realized in cardiac stimulation devices and systems that employ one or more leads.

A cardiac stimulation system of the present invention may be implemented to include features that overcome known weaknesses in conventional approaches. For example, the leads of a conventional pacemaker or ICD are considered by many of those skilled in the art to be a "weak link" of such systems. Conventional leads, for example, are known to be prone to fatigue failures. Such leads can be prone to insulation failures, typically due to abrasion. Leads can sometimes cause permanent occlusion of the veins, and can be difficult to extract during an explant procedure.

According to embodiments of the present invention, an intrathoracic cardiac stimulation (ICS) system may be implemented as a leadless system. An ICS system may further be implemented in a distributed manner, such that multiple cardiac stimulation devices operate cooperatively to deliver cardiac stimulation therapy, such as a pacing or resynchronization therapy. By way of example, an ICS system may be implemented to include two or more essentially autonomous but interactive ICS devices implanted in two or more heart chambers. Each of the ICS devices are preferably leadless devices, and each includes a power source (e.g., long-life battery or an externally rechargeable battery), control and other electronics, and electrodes configured to provide for cardiac activity sensing and energy delivery in a stand-alone manner, independent from other ICS devices of the system. Each of the ICS devices further includes communication circuitry that facilitates communication between individual ICS devices of the system. A communication link established between ICS devices is typically a bi-directional communication link, but certain configurations may provide for uni-directional communication as between a coordinating ICS device and a subordinate ICS device.

In accordance with various embodiments, an ICS device of the present invention is operable to provide essentially autonomous cardiac sensing and energy delivery, yet operates in concert with other ICS devices in accordance with an energy delivery protocol, such as a pacing, resynchronization, antitachycardia pacing, rate smoothing or regularization pacing, or defibrillation/cardioversion protocol or regimen. According to various apparatus embodiments, an ICS device includes a housing configured for intrathoracic placement relative to a patient's heart. The ICS device incorporates a fixation arrangement supported by the housing and configured to affix the housing at an implant location within cardiac tissue or cardiac vasculature. An electrode arrangement is supported by the housing and configured to sense cardiac activity and deliver stimulation energy to the cardiac tissue or cardiac vasculature. The ICS device includes energy delivery circuitry provided in the housing and coupled to the electrode arrangement. Energy produced by the energy delivery circuitry may be pacing energy, defibrillation/cardioversion energy, or non-excitory/sub-threshold energy (e.g., for impedance testing, increasing cardiac contractility, reversal of remodeling), for example.

The ICS device further includes detection circuitry provided in the housing and coupled to the electrode arrangement. Communications circuitry is supported by the housing. A controller is provided in the housing and coupled to the communications circuitry, energy delivery circuitry, and detection circuitry. The controller coordinates the operation of the ICS device and further coordinates delivery of energy to the cardiac tissue or cardiac vasculature in accordance with an energy delivery protocol appropriate for the implant location. In a system deployment involving two or more ICS devices, the controllers of the ICS devices communicate by way of a communications link established via each device's communications circuitry.

Although inter-device communication is considered advantageous, it is envisioned in certain embodiments that some or all of the ICS devices can have a simplified configuration, in which communications circuitry is excluded and the controllers of the simplified ICS devices are programmed to deliver energy to cardiac tissue in response to predetermined cardiac signals sensed by each of the simplified ICS devices. In a variation of this embodiment, one of the ICS devices may incorporate communications circuitry for effecting communication with a patient-external system, such as a programmer or interface to a networks server (e.g., a server of an advanced patient management system). This ICS device may incorporate memory for storing cardiac activity data and other data that can be transmitted to the external system.

The housing may be configured to assume a wide variety of shapes and geometries, such as by having a generally egg shape configuration, by way of non-limiting example. The housing may include one or more recesses or other arrangement configured to receive a distal portion of an implantation drive member. The housing may also include an arrangement, such as a locking arrangement, that couples to a wire or other explant member that facilitates extraction of the ICS device. In the case of an intravenous configuration, the housing may include one or more channels configured to facilitate perfusion of blood through or around the housing. For example, the housing may include a single or multiple bores through which blood may pass. The housing may include channels or flutes to facilitate blood perfusion.

The electrode arrangement of the ICS device may be configured as an epicardial, endocardial, or intravenous electrode arrangement. In one configuration, the electrode arrangement may include one or more annular electrodes supported circumferentially about all or a portion of the housing. The electrode arrangement may incorporate an annular electrode supported circumferentially about at least a portion of the housing and a helical electrode extending from the housing. The electrode arrangement is preferably configured as a bipolar electrode arrangement.

The fixation arrangement of the ICS device may include one or more of a helical screw, tines, or other acute fixation arrangement. The fixation arrangement may also incorporate one or more chronic fixation arrangements that promote ingrowth or adhesion with cardiac tissue. The fixation arrangement of the ICS device may define an anode or cathode of the electrode arrangement, such as in the case of a helical fixation electrode. In other configurations, the fixation arrangement may be electrically isolated from the electrode arrangement. In the case of a transvenous implementation, the fixation arrangement may include one or more fixation members configured to extend outwardly from the housing and engage an inner surface of a cardiac vessel. Such fixation members may be formed from a suitable polymeric material.

An ICS device may be configured to provide only cardiac activity sensing, but finds particular usefulness when configured to provide both cardiac activity sensing and energy delivery capabilities. One, two, or more ICS devices may be configured to cooperatively implement a cardiac rhythm management regimen, such as a pacing regime, wherein individual ICS devices implement a portion of the cardiac rhythm management regimen. By way of example, a first ICS device may be implanted in a patient's right atrium, and a second ICS device may be implanted in the patient's right ventricle. A cardiac rhythm management regimen may be implemented by the first and second ICS devices operating cooperatively, such that the first and second ICS devices respectively deliver pacing pulses to the right atrium and ventricle at appropriate times as dictated by the cardiac rhythm management regimen. As such, each ICS device performs sensing and energy delivery operations appropriate for the device's specific implant location (right atrium or right ventricle in this illustrative example), and the coordinated sensing and energy delivery operations of all ICS devices implement a given cardiac rhythm management regimen.

Accordingly, the energy delivery protocol implemented by an ICS device may be a pacing protocol appropriate for a specific chamber of the heart, a multiple chamber pacing protocol, such as a resynchronization pacing protocol, or a multisite pacing protocol, whereby at least two ICS devices are implanted in the same heart chamber. The energy delivery protocol implemented by one or more ICS devices may be a defibrillation or cardioversion protocol. The energy delivery protocol implemented by one or more ICS devices may also include delivery of stimulation energy insufficient to effect capture, such as for impedance testing or improving cardiac contractility.

The communications circuitry provided in a given ICS device is typically configured to facilitate communication between the ICS device and one or more other ICS devices. The communications circuitry of one or more ICS devices is typically configured to effect communication with a patient-external system, such as a patient-external receiver or transceiver, programmer, or communications interface of a patient management system, for example. As discussed previously, the communications link between ICS devices is typically bi-directional, but may be uni-directional as between particular ICS devices. The communication link between one or more ICS devices and a patient-external system is typically bi-directional, but may be uni-directional in particular applications.

An ICS system (i.e., one or more ICS devices) may be configured to sense cardiac activity and detect adverse cardiac events or conditions, such as one or more of cardiac arrhythmia (e.g., bradycardia, tachycardia, fibrillation), post-shock asystole, and poor cardiac output, for example. An ICS system of the present invention may be configured to deliver one or more therapies to treat detected cardiac events or conditions, including tachycardia prevention therapy (e.g., antitachycardia pacing therapy, cardioversion therapy, defibrillation therapy), bradycardia prevention therapy, and an asystole prevention therapy. In response to detecting an adverse cardiac event or condition requiring treatment, the ICS system determines which of several available therapies is appropriate to treat the subject event or condition and delivers an appropriate therapy.

Turning now to FIGS. 1A-1D, there is illustrated four configurations of an ICS system in accordance with embodiments of the present invention. FIG. 1A is a depiction of a heart 100, with an intrathoracic cardiac stimulation device 102 implanted in the right atrium (RA) of a patient's heart. FIG. 1A illustrates a single chamber implementation of a leadless ICS system which can be configured to provide one or both of cardiac activity monitoring and energy delivery. The ICS device 102 shown in FIG. 1A may provide sensing and energy delivery functionality similar to that offered by conventional single chamber lead-based pacemakers or ICDs. Unlike such conventional devices, provision of ICS device 102 eliminates the need for lead implantation and associated long term reliability concerns, and further eliminates the need for a subcutaneous pocket incision for accommodating a convention can/housing. Implantation of ICS device 102 may be accomplished using a variety of techniques, including use of a screwdriver stylet for endocardial and epicardial implantation, for example. Explanting of ICS device 102 may, for example, be accomplished using a wire that engages a locking mechanism provided on the housing of the ICS device 102.

FIG. 1B shows an ICS system implementation in which an ICS device 102 is implanted in each of the right atrium and right ventricle (RV) of a patient's heart. FIG. 1B illustrates a dual chamber implementation of a leadless ICS system which can be configured to provide one or both of cardiac activity monitoring and energy delivery. The ICS devices 102 shown in FIG. 1B may provide sensing and energy delivery functionality similar to that offered by conventional dual chamber lead-based pacemakers or ICDs. In one approach, each of the ICS devices 102 is substantially the same in terms of construction, electronics, and functionality, which allows for a reduction in system complexity (e.g., reduced programming and interfacing complexity) and cost. In another approach, one of the ICS devices 102 is constructed as a coordinating ICS device and the other ICS device 102 is constructed as a subordinate ICS device. As such, the ICS devices 102 may differ substantially from one another in terms of construction, electronics, and functionality, examples of which will be discussed hereinbelow.

FIG. 1C shows an ICS system implementation in which an ICS device 102 is implanted in each of the right atrium, right ventricle, and left ventricle (LV) of a patient's heart. FIG. 1D shows an ICS system implementation in which an ICS device 102 is implanted in each of the right atrium, right ventricle, left ventricle, and left atrium (LA) of a patient's heart. FIGS. 1C and 1D are intended to illustrate multiple chamber implementations of a leadless ICS system which can be configured to provide one or both of cardiac activity monitoring and energy delivery. By way of example, the ICS systems shown in FIGS. 1C and 1D may be configured to provide bi-ventricular pacing therapies. By way of further example, the ICS systems shown in FIGS. 1C and 1D may be configured to provide resynchronization pacing therapies.

The ICS devices 102 shown in FIGS. 1C and 1D may provide sensing and energy delivery functionality similar to that offered by conventional multiple chamber lead-based pacemakers or ICDs. As in the case of the ICS systems depicted in FIG. 1B, each of the ICS devices 102 shown in FIGS. 1C and 1D may be substantially the same in terms of construction, electronics, and functionality. In other implementations, at least one of the ICS devices 102 may be constructed as a coordinating ICS device and the other ICS devices 102 may be constructed as subordinate ICS devices.

Multiple chamber embodiments of an ICS system described herein may be used in connection with congestive heart failure (CHF) monitoring, diagnosis, and/or therapy. Methods, structures, and/or techniques described herein relating to CHF, such as those involving dual-chamber or bi-ventricular pacing/therapy, cardiac resynchronization therapy, cardiac function optimization, or other CHF related methodologies, can incorporate features of one or more of the following references: commonly owned U.S. patent application Ser. No. 10/270,035, filed Oct. 11, 2002, entitled "Timing Cycles for Synchronized Multisite Cardiac Pacing;" and U.S. Pat. Nos. 6,411,848; 6,285,907; 4,928,688; 6,459,929; 5,334,222; 6,026,320; 6,371,922; 6,597,951; 6,424,865; and 6,542,775, which are hereby incorporated herein by reference. Various ICS system embodiments described herein may be used in connection with preferential pacing/rate regularization therapies. Methods, structures, and/or techniques described herein relating to such therapies, such as those involving single chamber, multi-chamber, multi-site pacing/therapy or other related methodologies, can incorporate features of one or more of the following references: commonly owned U.S. patent application Ser. No. 09/316,515, filed May 21, 1999, entitled "Method and Apparatus for Treating Irregular Ventricular Contractions Such As During Atrial Arrhythmia;" and U.S. Pat. Nos. 6,353,759 and 6,351,669, which are hereby incorporated herein by reference.

Figure 5:
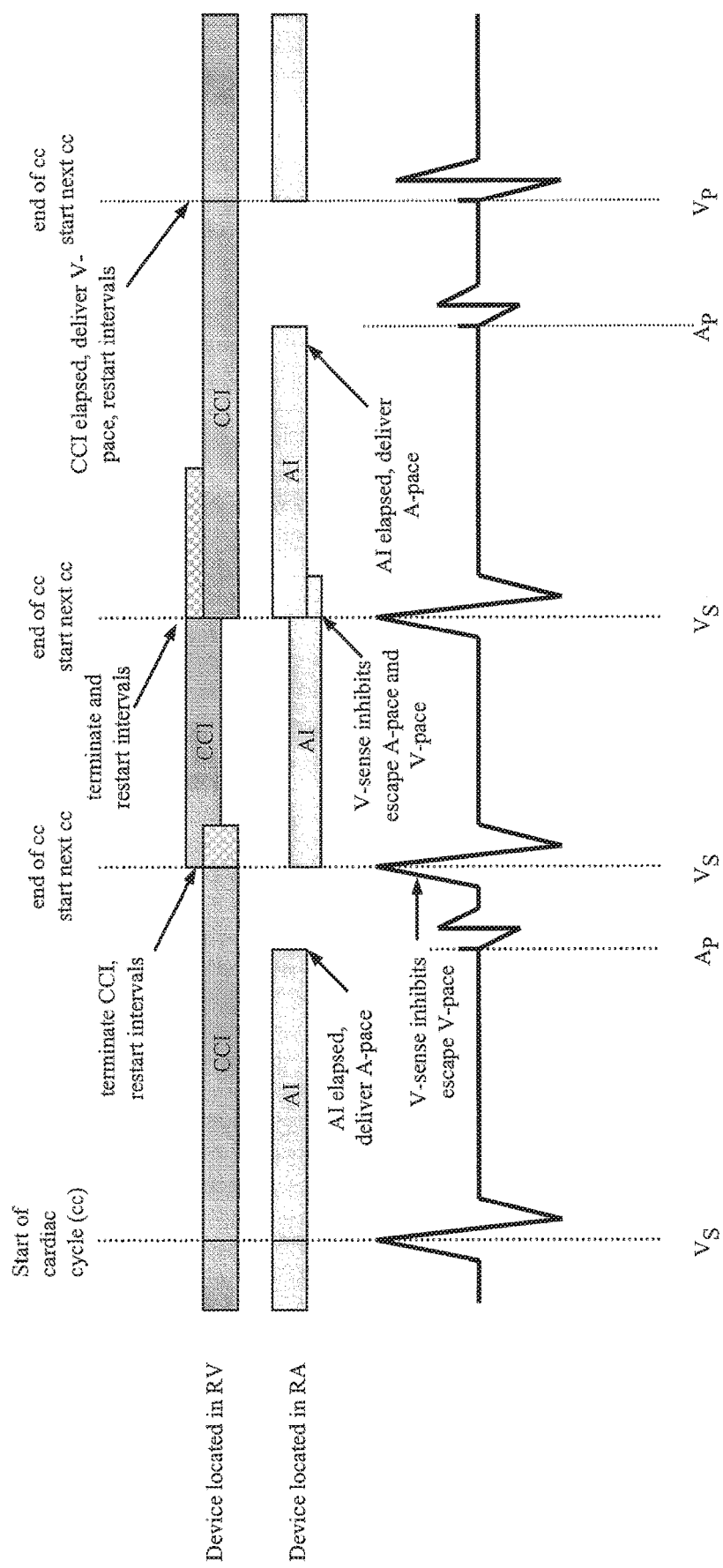
FIG. 5 is a timing diagram that represents one of many possible timing scenarios for pacing multiple chambers of the heart using an intrathoracic cardiac stimulation system of the present invention.

FIGS. 2A-2D illustrate a number of methodologies that facilitate communication between individual ICS devices and between ICS devices and patient-external systems. FIG. 2A illustrates four chambers of a heart 100. An ICS device 102 is shown implanted in three of the four heart chambers; the right atrium, right ventricle, and left ventricle. In one embodiment, each of the ICS devices 102 is equipped with communications circuitry that facilitates bi-directional communication between the respective ICS devices 102. In one illustrative example, each ICS device 102 senses for a particular cardiac event (e.g., an intrinsic event) and decides when to deliver cardiac stimulation energy based on the operative cardiac rhythm management regimen, specific location of the ICS device 102, and activity of other ICS devices 102. A timing diagram associated with one of many possible pacing regimens is illustrated in FIG. 5, for example.

FIG. 2B illustrates another embodiment involving inter-device 102 communications and communication between ICS devices 102 and a patient-external system 200. In FIG. 2B, a bi-directional communication link is established between an ICS device 102 implanted in a patient's right atrium and an ICS device 102 implanted in the patient's right ventricle. The communication link established between two or more ICS devices 102 may be a conventional radio frequency (RF) link that is traditionally used to effect communications between an implantable pulse generator and an external programmer as is known in the art. The communication link between ICS devices 102 may be implemented using a short-range wireless communication interface in each of the ICS devices 102, such as an interface conforming to a known communications standard, such as a Bluetooth standard, IEEE 802 standards (e.g., IEEE 802.11), or other public or proprietary wireless protocol. Other useful communication techniques and circuitry, aspects of which may be implemented by an ICS device of the present invention, are disclosed in U.S. Pat. No. 6,141,588, which is hereby incorporated herein by reference.

A non-electromagnetic communication link may also be employed to facilitate inter-device communication, such as a link that utilizes pressure waves encoded with data. One such approach employs piezoelectric transducers that generate and detect high-speed pressure waves, aspects of which are disclosed in U.S. Pat. No. 5,411,535, which is hereby incorporated herein by reference. It is noted that communications circuitry disposed in one or more ICS devices 102 may also facilitate unidirectional or bidirectional communication with one or more external, cutaneous, subcutaneous, or otherwise implantable physiologic or non-physiologic sensors (e.g., blood oxygen sensors, transthoracic impedance sensors, blood volume sensors, acoustic sensors and/or pressure transducers, and accelerometers). Information acquired by such sensors may be used to adjust a pacing or other energy delivery therapy deliverable be an ICS system.

Another mode of effecting a communication link involves use of low-voltage pulses encoded with data. The voltage and/or frequency (assuming a non-DC signal) is selected so as not to interfere with intrinsic or device-assisted pacing functions. Typically, the low-voltage encoded pulses are conducted via cardiac tissue and do not cause a reaction in the tissue.

In the embodiment shown in FIG. 2B, the communication interface provided in each ICS device 102 facilitates bi-directional communication between each ICS device 102 and a patent-external system 200. This communication link may be a conventional RF link or short-range wireless communication link as discussed above. Although a bi-directional communication link between an ICS device 102 and a patient-external system 200 is considered desirable, it is contemplated that certain patient-external systems 200 may require only a uni-directional communication link, as in the case of a patient activator that triggers a diagnostic or therapeutic function of the ICS system.

The patient-external system 200 may be an external programmer that incorporates a communications interface to provide for reception and transmission of signals and data between the external programmer and communications circuitry of the ICS devices 102. In this manner, programming commands and data may be transferred between the ICS devices 102 and the external programmer during and after implant. Using a programmer, a physician is able to set or modify various parameters used by the ICS devices 102. For example, a physician may set or modify parameters affecting sensing, detection, pacing, and defibrillation functions of the ICS devices 102, including pacing and cardioversion/defibrillation therapy modes. The patient-external system 200 may take other forms, such as a portable or bed-side communication station, patient-carried/worn communication station, patient management server-based system, or other communications or diagnostic system.

FIGS. 2C and 2D illustrate additional embodiments involving inter-device 102 communications and communication between ICS devices 102 and a patient-external system 200. In FIGS. 2C and 2D, the ICS devices 102 are of differing configuration. In particular, ICS device 102A is implemented as a coordinating ICS device and ICS device 102B is implemented as a subordinate ICS device. As shown, ICS device 102A incorporates communication circuitry that facilitates communication with the patient-external system 200, while ICS device 102B excludes this communication capability. A bi-directional communication link between ICS devices 102A and 102B provides for inter-device communications. External access to the subordinate ICS device 102B by the patient-external system 200 may be effected by way of the bi-directional communication link between the coordinating ICS device 102A and the patient-external system 200 and the bi-directional communication link between the coordinating ICS device 102A and the subordinate ICS device 102B. As such, the communications facility of the coordinating ICS device 102A may be used as a communications router, in that access to one or more subordinate ICS devices 102B may be achieved via the coordinating ICS device 102A. It is noted that an ICS system may include one or more coordinating ICS devices 102A and one or more subordinate ICS devices 102B.

In FIG. 2D, ICS device 102A incorporates communication circuitry that facilitates bi-directional communication with the patient-external system 200, while ICS device 102B excludes this communication capability. A uni-directional communication link is established between the coordinating ICS device 102A and the patient-external system 200 in this embodiment. Although a bi-directional communications link between ICS devices 102A and 102B is generally desirable, certain ICS system implementations may allow for a reduced level of inter-device communication, thus allowing for a more simplified inter-device communication strategy. External access to the subordinate ICS device 102B by the patient-external system 200 may be effected via the bi-directional communication link between the coordinating ICS device 102A and the patient-external system 200 and the uni-directional communication link between the coordinating ICS device 102A and the subordinate ICS device 102B.

FIG. 3A illustrates an ICS device 300A configured for endocardial or epicardial implantation that provides cardiac pacing therapy in accordance with an embodiment of the present invention. In this illustrative embodiment, the ICS device 300A includes a housing 302 that supports an electrode arrangement and an antenna arrangement. The electrode arrangement according to this embodiment includes an annular electrode 306, operative as an anode of the electrode arrangement, and a fixation screw 304, operative as a cathode of the electrode arrangement. An antenna 308 (e.g., an RF antenna) is configured as a ring supported on the housing 302. It is noted that the annular electrode 306 and annular antenna 308 may take on other shapes and geometries depending on the shape or geometry of the housing 302.

It is noted that the electrode arrangement and/or the housing may incorporate a mechanism for delivering or eluting a steroid or other pharmacological agent, typically for purposes of reducing voltage thresholds. Such mechanisms may include a coating or sleeve disposed on the electrode that contains a steroid or other pharmacological agent. Other systems and materials useful for drug delivery in accordance with the present invention are further described in commonly owned U.S. Pat. Nos. 4,819,662 and 6,361,780, which are hereby incorporated herein by reference. It is further noted that the electrode arrangement may include a fractal electrode coating, such as one that comprises iridium oxide, as is known in the art.

A recess 307 is provided on the housing 302 and configured to receive a drive member, such as a stylet. For example, the recess 307 may be a key-hole that receives a drive member having an appropriate size and shape. The recess 307 or other arrangement may be configured to couple with a wire or other member for purposes of extracting the ICS device 300A from the heart. This coupling arrangement may include a locking mechanism that engages an extraction member during an explant procedure.

FIG. 3B illustrates an ICS device 300B configured for transvenous implantation that provides cardiac pacing therapy in accordance with an embodiment of the present invention. In this illustrative embodiment, the ICS device 300B includes a pair of annular electrodes 306A, 306B that respectively define an anode and a cathode of the ICS device's electrode arrangement. An annular antenna 308 is provided on the housing 302. The ICS device 300B also includes a fixation arrangement that includes one or more fixation members 312 configured to extend outwardly from the housing 302 and engage an inner surface of a cardiac vessel. In the embodiment of FIG. 3B, two such fixation members 312 are shown. The fixation members 312 may be polymeric rings of a diameter greater than that of the housing 302. The polymeric rings 312 are sufficiently flexible to allow for some deformation during implantation, yet have sufficient strength to resist deflection in response to forces associated with blood flow once situated at an implant site.

The fixation members 312 may be perforated to allow for blood perfusion. The housing 302 may also include one or more bores 314 to facilitate perfusion of blood through the housing 302. The housing 302 may alternatively, or additionally, include channels or flutes that allow for perfusion of blood around the housing 302. The housing 302 may incorporate an occlusion arrangement, such as one or more inflatable occlusion balloons or flutes, that can be actuated during implantation, but retracted/deactivated after implantation. Such an occlusion mechanism may be used in connection with an implant procedure within a cardiac vessel, whereby a radio-opaque dye is injected into the vessel for purposes of locating the housing 302 during implant as is known in the art.

The central bore 314 shown in FIG. 3B may include a recessed or shaped portion configured to receive a drive member for purposes of implantation. A coupling arrangement may be built into the central bore 314 or elsewhere on the housing 302 and configured to receive a wire or other member for purposes of extracting the ICS device 300B from the heart. As in the previous embodiment, this coupling arrangement may include a locking mechanism that engages an extraction member during an explant procedure. A transvenous stimulation apparatus and method, aspects of which may be implemented by an ICS device of the present invention, are disclosed in U.S. Pat. No. 6,445,953, which is hereby incorporated herein by reference.

FIG. 3C illustrates an intrathoracic cardiac stimulation device configured for endocardial or epicardial implantation that provides one or both of cardiac defibrillation and cardioversion therapy, alone or with pacing therapy, in accordance with an embodiment of the present invention. In this embodiment, the housing 302 includes a fixation screw 304 and an annular antenna 308. The housing 302 supports an annular electrode 306 and an elongated electrode 310. The annular electrode 306 and elongated electrode 310 operate as a defibrillation electrode pair for delivery of high energy cardioversion or defibrillation waveforms (e.g., mono-phasic, bi-phasic, or tri-phasic waveforms). The annular electrode 306 and elongated electrode 310 also operate as a sense electrode pair. The housing 302 may include a second annular electrode 306 that allows for bi-polar cardiac activity sensing and/or pacing, in which case the elongated electrode 310 may be used exclusively for delivering cardioversion or defibrillation therapy. A stimulation apparatus and method, aspects of which may be implemented by an ICS device of the present invention, are disclosed in U.S. Pat. No. 5,405,367, which is hereby incorporated herein by reference.

FIG. 4 is a block diagram of electronic circuitry and components of an ICS device 300 in accordance with an embodiment of the present invention. It is understood that the components and functionality depicted in FIG. 4 and described herein may be implemented in hardware, software, or a combination of hardware and software. It is further understood that the components and functionality depicted as separate or discrete blocks/elements in FIG. 4 may be implemented in combination with other components and functionality, and that the depiction of such components and functionality in individual or integral form is for purposes of clarity of explanation, and not of limitation.

As shown in FIG. 4, the ICS device 300 includes a housing 302 that supports a fixation arrangement 414, an electrode arrangement 410, and an antenna 413. Disposed within the housing 302 are a number of components, including a controller 402, memory 403, detection circuitry 404, energy delivery circuitry 406, and communications circuitry 412. The housing 302 also includes a power source 408, which may be a long-life electrochemical battery, a fuel cell, a rechargeable battery, or other energy source.

In one configuration, the power source 408 includes a rechargeable battery. According to this configuration, charging circuitry is coupled to the power source 408 to facilitate repeated non-invasive charging of the power source 408 from an external source. The communications circuitry 412, or separate receiver circuitry, is configured to receive RF energy transmitted by an external RF energy transmitter. The ICS device 300 may, in addition to a rechargeable power source, include a non-rechargeable battery. It is understood that a rechargeable power source need not be used, in which case a long-life non-rechargeable battery is employed. An ICS device 300 may incorporate power transmission and other control features disclosed in U.S. Pat. No. 5,814,089, which is hereby incorporated herein by reference.

Communications circuitry 412 is disposed within the housing 302 and facilitates communication between the ICS device 300 and an external communication device 200, such as a portable or bed-side communication station, patient-carried/worn communication station, or external programmer, for example. The communications circuitry 412 also facilitates unidirectional or bidirectional communication with one or more other ICS devices 302 of an ICS system. The communications circuitry 412 may further facilitate unidirectional or bidirectional communication with one or more external, cutaneous, subcutaneous, or otherwise implantable physiologic or non-physiologic sensors.

The controller 402 may includes a micro-processor coupled to appropriate memory 403 (volatile and non-volatile), it being understood that any logic-based control architecture may be used. The controller 402 is coupled to circuitry and components to sense, detect, and analyze electrical signals produced by the heart and deliver electrical stimulation energy to the heart under predetermined conditions to treat cardiac arrhythmias. In certain configurations, the controller 402 and associated components also provide pacing therapy to the heart. The electrical energy delivered by the energy delivery circuitry 406 of the ICS device 300 may be in the form of non-excitory energy, low energy pacing pulses, or high-energy pulses for cardioversion or defibrillation, for example.

Cardiac signals are sensed using the electrodes 410 provided on or supported by the ICS device housing 302. The sensed cardiac signals are received by detection circuitry 404, which includes sense amplification circuitry and may also include filtering circuitry and an analog-to-digital (A/D) converter. The sensed cardiac signals processed by the detection circuitry 404 may be received by noise reduction circuitry, which may further reduce noise content of the sensed cardiac signals.

Detection circuitry 404 may include a signal processor that coordinates analysis of the sensed cardiac signals and/or other sensor inputs to detect cardiac arrhythmias, such as, in particular, tachyarrhythmia. Rate based and/or morphological discrimination algorithms may be implemented by the signal processor of the detection circuitry 404 to detect and verify the presence and severity of an arrhythmic episode. Exemplary arrhythmia detection and discrimination circuitry, structures, and techniques, aspects of which may be implemented by an ICS device 300 of the present invention, are disclosed in commonly owned U.S. Pat. Nos. 5,301,677 and 6,438,410, which are hereby incorporated herein by reference. Tiered or parallel arrhythmia discrimination algorithms may also be implemented using both rate-based and morphologic-based approaches.

Further, a rate and pattern-based arrhythmia detection and discrimination approach may be employed to detect and/or verify arrhythmic episodes, such as by use of the approaches disclosed in U.S. Pat. Nos. 6,487,443; 6,259,947; 6,141,581; 5,855,593; and 5,545,186, which are hereby incorporated herein by reference.

The detection circuitry 404 communicates cardiac signal information to the controller 402. Memory circuitry 403 of the controller 402 contains parameters for operating in various sensing, pacing, and, if applicable, defibrillation modes, and stores data indicative of cardiac signals received by the detection circuitry 404. The memory circuitry 403 may also be configured to store historical ECG and therapy data, which may be used for various purposes and transmitted to an external receiving device as needed or desired.

In certain configurations, the ICS device 300 may include diagnostics circuitry (not shown). The diagnostics circuitry typically receives input signals from the detection circuitry 404. The diagnostics circuitry provides diagnostics data to the controller 402, it being understood that the controller 402 may incorporate all or part of the diagnostics circuitry or its functionality. The controller 402 may store and use information provided by the diagnostics circuitry for a variety of diagnostics purposes. This diagnostic information may be stored, for example, subsequent to a triggering event or at predetermined intervals, and may include system diagnostics, such as power source status, therapy delivery history, and/or patient diagnostics. The diagnostic information may take the form of electrical signals or other sensor data acquired immediately prior to therapy delivery.

An ICS device 300 may incorporate a cardiac pacing capability in addition to, or to the exclusion of, cardioversion and/or defibrillation capabilities. The ICS device 300 may include pacing therapy circuitry within the energy delivery circuitry 406, which is coupled to the controller 402 and the electrodes 410. Upon command, the pacing therapy circuitry delivers pacing pulses to the heart in accordance with a selected pacing therapy. Control signals, developed in accordance with a pacing regimen by pacemaker circuitry within the controller 402, are initiated and transmitted to the pacing therapy circuitry where pacing pulses are generated. A pacing regimen may be modified by the controller 402.

According to a configuration that provides cardioversion and defibrillation therapies, the controller 404 processes cardiac signal data received from the detection circuitry 404 and initiates appropriate tachyarrhythmia therapies to terminate cardiac arrhythmic episodes and return the heart to normal sinus rhythm. The controller 402 is coupled to shock therapy circuitry of the energy delivery circuitry 406. The shock therapy circuitry is coupled to electrodes 410. Upon command, the shock therapy circuitry delivers cardioversion and defibrillation stimulation energy to the heart in accordance with a selected cardioversion or defibrillation therapy. In a less sophisticated configuration, the shock therapy circuitry is controlled to deliver defibrillation therapies, in contrast to a configuration that provides for delivery of both cardioversion and defibrillation therapies. Exemplary ICD high energy delivery circuitry, structures and functionality, aspects of which may be incorporated in an ICS device 300 of a type that may benefit from aspects of the present invention are disclosed in commonly owned U.S. Pat. Nos.: 5,372,606; 5,411,525; 5,468,254; and 5,634,938, and in 5,133,353; 5,179,945; 5,314,459; 5,318,597; 5,620,466; and 5,662,688, which are hereby incorporated herein by reference.

In particular configurations, systems and methods may perform functions traditionally performed by pacemakers, such as providing various pacing therapies as are known in the art, in addition to cardioversion/defibrillation therapies. Exemplary pacemaker circuitry, structures and functionality, aspects of which may be incorporated in an ICS device of the present invention, are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference.

An ICS device in accordance with the present invention may implement diagnostic and/or monitoring functions as well as provide cardiac stimulation therapy. Exemplary cardiac monitoring circuitry, structures and functionality, aspects of which may be incorporated in an ICS device of the present invention, are disclosed in commonly owned U.S. Pat. Nos. 5,313,953; 5,388,578; and 5,411,031, which are hereby incorporated herein by reference in their respective entireties.

The components, functionality, and structural configurations described with reference to FIG. 4 are intended to provide an understanding of various features and combination of features that may be incorporated in an ICS device 300. It is understood that a wide variety of ICS and other implantable cardiac monitoring and/or stimulation device configurations are contemplated, ranging from relatively sophisticated to relatively simple designs. As such, particular ICS or cardiac monitoring and/or stimulation device configurations may include particular features as described herein, while other such device configurations may exclude particular features described herein.

An ICS device of the present invention may be used within the structure of an advanced patient monitoring (APM) system. APM systems may allow physicians to remotely and automatically monitor cardiac and respiratory functions, as well as other patient conditions. In one example, an ICS device or system may be equipped with various telecommunications and information technologies that enable real-time data collection, diagnosis, and treatment of the patient. Various embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

FIG. 5 is a timing diagram that represents one of many possible timing scenarios for pacing multiple chambers of the heart using a leadless intrathoracic cardiac stimulation system of the present invention. FIG. 5 shows several representative actions taken by multiple ICS devices in response to cardiac events sensed by the ICS devices. These actions are provided to illustrate aspects of cooperative pacing by use of multiple ICS devices. It is to be understood that a broad spectrum of pacing protocols/regimens may be implemented by use of multiple ICS devices of the present invention, ranging from relatively simple (e.g., as shown in FIG. 5) to relatively complex (e.g., resynchronization pacing).

In various embodiments, a pacing regimen may be effected by a multiplicity of ICS devices, wherein each of the ICS devices is configured to respond to certain cardiac signals independent from other ICS devices. In such embodiments, the ICS devices need not include communications circuitry to effect communication as between ICS devices for purposes of coordinating a distributed pacing regimen. Rather, each ICS device is programmed to deliver pacing pulses in accordance with an energy delivery protocol appropriate for its implant location. In this configuration, pacing logic is distributed among the ICS devices in a manner appropriate for implementing an overall pacing regimen for the patient. As discussed previously, it may be desirable that at least one of the ICS devices be configured with communications circuitry to effect communication between the ICS device and an external system.

In other embodiments, a pacing regimen may be effected by a multiplicity of ICS devices, wherein each of the ICS devices is configured to respond to certain cardiac signals yet communicate with other ICS devices. In such embodiments, the ICS devices include communications circuitry to effect communication as between ICS devices for purposes of coordinating a distributed pacing regimen. In this configuration, pacing logic is distributed among the ICS devices in a manner appropriate for implementing an overall pacing regimen for the patient, and communication between ICS devices may enhance implementation of such pacing regimen. Communication between ICS devices may provide for implementation of more sophisticated pacing regimens, such as bi-ventricular or resynchronization pacing therapies.

The following illustrative example describes a coordinated pacing methodology by use of multiple ICS devices that operate independently from one another, but together implement a dual chamber pacing regiment. In this illustrative example, it is assumed that the ICS devices do not communicate with one another to implement a dual chamber pacing regimen. As previously discussed one of the ICS may optionally incorporate communications circuitry to facilitated communications with a patent-external system.

According to this illustrative example, and with reference to the timing scenario of FIG. 5, it is assumed that a first ICS device is implanted in a patient's right ventricle and a second ICS device is implanted in the patient's right atrium. During each cardiac cycle, each of the first and second ICS devices "listens" (e.g., senses) for cardiac activity applicable to the heart chamber in which the particular ICS device is implanted. In response to detecting certain cardiac events, each of the first and second ICS device implements its particular pacing protocol.

The timing diagram of FIG. 5 shows three complete cardiac cycles (cc). The first cardiac cycle is initiated in response to the first ICS device sensing depolarization (e.g., an R-wave) of the right ventricle, which restarts a ventricular escape interval (CCI or cardiac cycle interval). The second ICS device also senses the right ventricular depolarization event, which causes initiation of an atrial escape interval (AI or atrial interval).

In the first complete cardiac cycle shown in FIG. 5, it can be seen that the second ICS device delivers a pace to the right atrium in response to expiration of the AI interval. The first ICS device senses an intrinsic RV depolarization prior to expiration of the ventricular escape interval (CCI), which inhibits delivery of a right ventricular pace by the first ICS device and restarts the escape interval timing of the first and second ICS devices (e.g., restarts the CCI and AI intervals).

In the second full cardiac cycle, which is initiated by a V-sense at the end of the first cardiac cycle, a second V-sense event is sensed by the first ICS device prior to the second ICS device sensing an atrial depolarization. This scenario can occur in the case of a premature ventricular contraction (PVC), in which two consecutive ventricular depolarization events occur in the absence of an intervening atrial depolarization event. In this case, sensing of the V-sense event by the first ICS device results in inhibiting delivery of a V-pace by the first ICS device and an A-pace by the second ICS device, terminates the current ventricular escape interval (CCI), and restarts the pace timing of the first and second ICS devices.

In the third full cardiac cycle, the first ICS device senses a V-sense event and restarts the ventricular escape interval (CCI). The second ICS device also senses the V-sense event and restarts the atrial escape interval (AI). In this cardiac cycle, expiration of the atrial escape interval results in delivery of an A-pace by the second ICS device. Expiration of the ventricular escape interval results in delivery of a V-pace by the first ICS device. The next cardiac cycle is then initiated upon delivery of the V-pace, which results is restarting of the atrial and ventricular escape intervals for the next cardiac cycle.

The following illustrative example describes a coordinated pacing methodology by use of multiple ICS devices that are equipped with communications circuitry to effect communications there between. According to this illustrative example, and with continued reference to the timing scenario of FIG. 5, it is assumed that a first ICS device is implanted in a patient's right ventricle and a second ICS device is implanted in the patient's right atrium. The first cardiac cycle is initiated in response to the first ICS device sensing depolarization of the right ventricle, which restarts a ventricular escape interval (CCI or cardiac cycle interval). A signal is communicated from the first ICS device to the second ICS device causing the second ICS device to restart an atrial escape interval (AI or atrial interval).

In the first complete cardiac cycle shown in FIG. 5, the second ICS device delivers a pace to the right atrium in response to expiration of the AI interval. The first ICS device senses an intrinsic RV depolarization prior to expiration of the ventricular escape interval (CCI), which inhibits delivery of a right ventricular pace by the first ICS device and restarts the escape interval timing of the first and second ICS devices. It is noted that, in a more complex pacing scenario, the second ICS device could transmit a signal to the first ICS device in response to delivery of the A-pace at the expiration of the AI interval. The first ICS device, in response, could initiate an AV interval that could be shorter or longer than the CCI interval, thus allowing for atrial tracking functionality (e.g., metabolic rate-based pace timing).

In the second full cardiac cycle, which is initiated by a V-sense at the end of the first cardiac cycle, a second V-sense event is sensed by the first ICS device prior to the second ICS device sensing an atrial depolarization. In this case, sensing of the V-sense event by the first ICS device results in inhibiting delivery of a V-pace by the first ICS device and an A-pace by the second ICS device, terminates the current ventricular escape interval (CCI), and restarts the pace timing of the first and second ICS devices.

In the third full cardiac cycle, the first ICS device senses a V-sense event, restarts the ventricular escape interval (CCI), and communicates a signal to the second ICS device causing restarting of the atrial escape interval (AI). In this cardiac cycle, expiration of the atrial escape interval results in delivery of an A-pace by the second ICS device. Expiration of the ventricular escape interval results in delivery of a V-pace by the first ICS device. The next cardiac cycle is then initiated upon delivery of the V-pace, which results is restarting of the atrial and ventricular escape intervals for the next cardiac cycle.

As was discussed previously, each of the ICS devices of a multiple ICS device system may be substantially the same or different in terms of construction, components, and functionality. Within the context of the timing scenario of FIG. 5, the first and second ICS devices may be essentially the same in construction, but obviously differ in terms of their sense/energy delivery timing protocol as appropriate for their particular heart chamber implant location. In one approach, no communication link exists between the two ICS devices. In another approach, a communication link exists between the two ICS devices that may be uni-directional or bi-directional. In one configuration, for example, each ICS device may communicate pacing event/timing signals to other ICS devices to implement a multi-device, distributed pacing protocol or regimen.

In another approach, one of the ICS devices may coordinate cardiac pacing to a greater extent than other ICS devices of an ICS system. In the context of the pacing scenario depicted in FIG. 5, for example, the first ICS device implanted in the right ventricle may be considered a coordinating ICS device, in that cardiac pacing timing of the first and second ICS devices is registered with respect to right ventricular events (i.e., ventricular depolarization events or lack thereof). In one implementation, the communication link between the first and second ICS devices may be uni-directional, wherein atrial escape interval restarting is initiated by the second ICS device in response to an AI restart signal received from the first ICS device. The second ICS device, which may be viewed as a subordinate ICS device in this illustrative example, need not communicate timing related signals to the first ICS device to implement the relatively simplistic pacing timing shown in FIG. 5.

In accordance with a further approach, as discussed above, it may be desirable to eliminate the communication link between the first and second ICS devices to implement a particular pacing protocol. In the context of the pacing timing diagram of FIG. 5, for example, the second ICS device located in the right atrium may be configured to be highly sensitive to the R-waves generated by ventricular depolarization events. In such a configuration, the second ICS device may be configured to detect R-waves and implement its pacing timing based on detected R-waves. In this example, the first and second ICS devices operate completely autonomously, in that the two devices are not communicatively coupled by a communication link, yet operate cooperatively to implement a given pacing regimen.

Various modifications and additions can be made to the embodiments discussed hereinabove without departing from the scope of the present invention. Accordingly, the scope of the present invention should not be limited by the particular embodiments described above, but should be defined only by the claims set forth below and equivalents thereof.

What is claimed is:
1. A leadless cardiac pacemaker (LCP) comprising:
   a housing configured for implantation in a patient's heart, the housing having a first end and an opposing second end;
   a fixation arrangement adjacent the first end of the housing, the fixation arrangement including one or more tines that are configured to fix the housing to cardiac tissue at an implant site within the patient's heart;

an explant assist feature adjacent the second end of the housing for engaging an extraction member to aid in explanting the LCP from the implant site, wherein the explant assist feature comprises a recess in the housing that is configured to couple with at least part of the extraction member to allow the extraction member to pull the LCP out of the cardiac tissue;

two or more electrodes, at least one of the electrodes adjacent the first end of the housing and at least one of the electrodes being an annular electrode adjacent the second end of the housing;

energy delivery circuitry situated in the housing and operatively coupled to two or more of the electrodes for delivering pacing therapy to the patient's heart;

detection circuitry situated in the housing and operatively coupled to two or more of the electrodes for detecting cardiac electrical activity of the patient's heart;

communications circuitry in the housing; and controller circuitry situated in the housing and operatively coupled to the energy delivery circuitry, the detection circuitry and the communications circuitry, the controller circuitry configured to deliver pacing therapy to the patient's heart via the energy delivery circuitry based at least in part on the detected cardiac electrical activity from the detection circuitry.

2. The LCP of claim 1, wherein the controller circuitry is configured to communicate with another device via the communications circuitry.

3. The LCP of claim 1, wherein the controller circuitry is configured to communicate with another device via conducted communication that uses encoded pulses that are conducted via the patient's body but are low enough energy to not cause capture of the patient's heart.

4. The LCP of claim 1, wherein the explant assist feature comprises a coupling arrangement that is configured to receive at least part of the extraction member.

5. The LCP of claim 1, wherein the one or more tines of the fixation arrangement are separate from each of the two or more electrodes.

6. The LCP of claim 1, wherein the housing is configured to be transvenously delivered to the implant site.

7. The LCP of claim 1, wherein the communications circuitry is configured to communicate with an external programmer via a first established communication link, and to communicate with a remote implanted device via a second established communication link.

8. The LCP of claim 7, wherein the communications circuitry is configured to route communications from the external programmer to the remote implanted device via the first established communication link and the second established communication link.

9. The LCP of claim 8, wherein the communications circuitry is configured to route communications from the remote implanted device to the external programmer via the second established communication link and the first established communication link.

10. The LCP of claim 8, wherein the first established communication link is bi-directional and the second established communication link is bi-directional.

11. The LCP of claim 1, wherein the communications circuitry is configured to communicate with a remote implanted device via an established communication link.

12. The LCP of claim 11, wherein the controller circuitry is configured to deliver pacing therapy to the patient's heart via the energy delivery circuitry based at least in part on the detected cardiac electrical activity from the detection circuitry and one or more cardiac parameters communicated from the remote implanted device via the established communication link.

13. The LCP of claim 12, wherein the one or more cardiac parameters include timing of an intrinsic and/or a paced beat in another chamber of the patient's heart from the chamber of the implant site of the LCP.

14. A leadless cardiac pacemaker (LCP) comprising:
a housing configured for transvenous delivery and implantation in a patient's heart, the housing having a first end and an opposing second end;

one or more acute tines secured to and extending from the housing and configured to extend into and fix the housing to a cardiac wall of the patient's heart at an implant site;

two or more electrodes supported by the housing, at least one of the electrodes extending annularly around the housing;

energy delivery circuitry situated in the housing and operatively coupled to two or more of the electrodes for delivering pacing therapy to the patient's heart;

detection circuitry situated in the housing and operatively coupled to two or more of the electrodes for detecting cardiac electrical activity of the patient's heart;

communications circuitry in the housing, the communications circuitry configured to use encoded pulses that are conducted via the patient's body but are low enough energy to not cause capture of the patient's heart; and controller circuitry situated in the housing and operatively coupled to the energy delivery circuitry, the detection circuitry and the communications circuitry, the controller circuitry configured to deliver pacing therapy to the patient's heart via the energy delivery circuitry based at least in part on the detected cardiac electrical activity from the detection circuitry.

15. The LCP of claim 14, wherein the communications circuitry is configured to communicate with a remote implanted device via an established communication link.

16. The LCP of claim 15, wherein the controller circuitry is configured to deliver pacing therapy to the patient's heart via the energy delivery circuitry based at least in part on the detected cardiac electrical activity from the detection circuitry and one or more cardiac parameters communicated from the remote implanted device via the established communication link.

17. A system comprising
a first implantable medical device implanted at a first implant site in a patient's heart;
a second implantable medical device implanted at a second implant site in a patient's heart;
an external device external to the patient's body;
the first implantable medical device is configured to directly communicate with the second implantable medical device;
the external device is configured to communicate directly with the first implantable medical device;
the external device is configured to not communicate directly with the second implantable medical device; and
the external device is configured to communicate with the second implantable medical device via the first implantable medical device, where the first implantable medical device acts as a communication router.

18. The system of claim 17, wherein:
the first implantable medical device is configured to directly communicate in a bi-directional manner with the second implantable medical device; and
the external device is configured to communicate directly in a bi-directional manner with the first implantable medical device.

19. The system of claim 18, wherein the first implantable medical device comprises a leadless cardiac pacemaker (LCP) implanted in a first chamber of the patient's heart, and wherein the second implantable medical device comprises a leadless cardiac pacemaker (LCP) implanted in a second chamber of the patient's heart.

* * * * *